United States Patent [19]
Grandjean et al.

[11] Patent Number: 6,046,274
[45] Date of Patent: Apr. 4, 2000

[54] FLEXIBLE COMPOSITION BASED ON VINYL CHLORIDE POLYMER, USE OF SAID COMPOSITION FOR MANUFACTURING ARTICLES AND ARTICLES MADE OF SAID COMPOSITION

[75] Inventors: Dominique Grandjean, Vilvoorde; Zdenek Hruska, Brussels; Danny Van Hoyweghen, Heverlee; Henri Wautier, Braine-le-Comte, all of Belgium

[73] Assignee: Solvay (Societe Anonyme), Brussels, Belgium

[21] Appl. No.: 08/973,272

[22] PCT Filed: May 22, 1996

[86] PCT No.: PCT/EP96/02223

§ 371 Date: Jan. 28, 1998

§ 102(e) Date: Jan. 28, 1998

[87] PCT Pub. No.: WO96/38503

PCT Pub. Date: Dec. 5, 1996

[30] Foreign Application Priority Data

Jun. 2, 1995 [BE] Belgium .................................. 9500489

[51] Int. Cl.⁷ ........................... C08L 27/06; B32B 27/30; B65D 30/02

[52] U.S. Cl. ........................... 525/92 A; 525/88; 525/93; 524/505; 428/35.4; 428/522; 428/524

[58] Field of Search ............................... 525/92 A, 92 B, 525/88, 93; 524/505; 428/35.4, 524, 522

[56] References Cited

U.S. PATENT DOCUMENTS 3,312,753  4/1967  Bailey et al. .
3,689,531  9/1972  Critchfield et al. .
3,949,015  4/1976  Laverty et al. .

*Primary Examiner*—Mark L. Warzel
*Attorney, Agent, or Firm*—Venable

[57] ABSTRACT

The invention relates to a flexible composition comprising a vinyl chloride polymer and a block copolymer. The latter comprises a poly(ethylene oxide) block and a block of a polymer which is miscible with the vinyl chloride polymer, other than the latter itself. The invention also relates to a poly(ethylene oxide)/poly-ε-caprolactone diblock copolymer which can be used in this composition, as well as to the use of this composition for the manufacture of an article and to an article comprising this composition.

8 Claims, No Drawings

FLEXIBLE COMPOSITION BASED ON VINYL CHLORIDE POLYMER, USE OF SAID COMPOSITION FOR MANUFACTURING ARTICLES AND ARTICLES MADE OF SAID COMPOSITION

FIELD OF THE INVENTION

The present invention relates to a flexible composition comprising a vinyl chloride polymer and a block copolymer, to a use of this composition for the manufacture of an article and to an article comprising this composition.

TECHNOLOGY REVIEW

Flexible compositions based on vinyl chloride polymer have been used for a long time in the most diverse industrial applications. Applications may be mentioned, for example, in the building, automobile, decorating and medical accessory fields.

In the last field, it is particularly advantageous to have available materials which exhibit good compatibility and complete harmlessness with respect to biological tissues and medicinal principles with which these materials can come into contact.

The excellent properties of flexible poly(vinyl chloride), such as its high transparency, and the wide range in the degree of flexibility which may be made available with this material make it a very widely used constituent in many medical applications.

In order to improve the biocompatibility of polymeric materials such as poly(vinyl chloride), a number of processes have been developed.

Some of these processes resort to surface treatments, which treatments are physical or chemical in nature. For example, Patent Application EP-A-0,093,094 describes a process according to which the surface of the polymer to be treated is made more hydrophilic after a number of cycles in which it is brought into contact with solutions followed by evaporation of the solvent. This type of process, in which solvents are handled, is complicated and expensive to implement industrially.

Other types of processes resort to the incorporation of modifying agents in the formulation of the composition. Thus, Patent Application JP-A-01,181,873 describes a mixture of flexible poly(vinyl chloride) and of a block copolymer obtained by reaction of a polycarboxylic polyester with a polysiloxane polyol or polysiloxane polyamine. Similarly, an article (Tsai et al., Asaio Journal (1994), Vol. 40, No. 3, pp. M619–M624) describes a poly-$\epsilon$-caprolactone/polydimethylsiloxane/poly-$\epsilon$-caprolactone block copolymer incorporated in a vinyl chloride polymer flexible composition.

However, while this last type of surface modification improves the compatibility of poly(vinyl chloride) with biological tissues and blood in particular, it does not guarantee perfect neutrality with respect to these. In particular, the adsorption of some components, such as proteins or blood cells, remains too high. This causes a decrease in their true concentration in the medium when the latter is brought into contact with the polymeric surface. Now, in many applications, it is essential that the concentration of certain components, including proteins in particular, in solutions or in tissues remains constant with time. It is also important that the additives employed in these formulations exhibit a minimum desorption when they are brought into contact with a biological tissue.

SUMMARY OF THE INVENTION

The subject of the invention is therefore a vinyl chloride polymer flexible composition which makes it possible to bring this composition into contact with media comprising organic macromolecules, more particularly proteins or peptides, without substantial adsorption of the latter at the surface of the composition nor significant desorption of its consituents.

The invention consequently relates to a flexible composition comprising a vinyl chloride polymer and a block copolymer which is characterized in that the block copolymer is chosen from copolymers comprising a poly(ethylene oxide) block and a block of a polymer which is miscible with the vinyl chloride polymer, other than the latter itself.

DETAILED DESCRIPTION OF THE INVENTION

Vinyl chloride polymer is understood to denote any vinyl chloride homopolymer, any vinyl chloride copolymer, and mixtures of these homo- and/or copolymers. Homopolymers have given very good results.

The composition is said to be flexible when it additionally comprises a substantial amount of plasticizer, in particular at least 20 parts of plasticizer per 100 parts of vinyl chloride polymer (by weight). Any type of plasticizer can be employed, the amount present obviously being adjusted in consequence. For example, alkyl phthalates, citrates, trimellitates and phosphates are widely employed. The plasticizer used can also be polymeric, which has the advantage of reducing its exudation. The plasticizer can also be provided, for example, in the form of side groups or chains grafted onto the vinyl chloride polymer.

Block copolymer denotes any polymer composed of at least two types of distinct monomers and which exhibits at least one long sequence of at least one of the monomers. The block copolymers which can be used in the context of the invention can be of any type. Linear block copolymers are, however, preferred. Diblock copolymers have provided excellent results. The use of mixtures of different block copolymers also comes within the scope of this invention.

The relative amount of block copolymer according to the invention in the composition is not limited. The Applicant Company has, however, observed that it was preferable to use a concentration of at least 0.5 parts per 100 parts by weight of plasticized vinyl chloride polymer, more preferentially of at least 1 part and more preferentially still of at least 3 parts. This concentration is advantageously of at most 10 parts per 100 parts of plasticized vinyl chloride polymer, more advantageously of at most 8 parts and more advantageously still of at most 6 parts.

A block is said to be composed of poly(ethylene oxide) if it contains a long sequence of repeat units of formula $(O-CH_2-CH_2)_n$. The poly(ethylene oxide) block can have any length but an average molecular mass at least equal to 500 g/mol and more particularly still to 3000 g/mol is preferred (all the molecular masses specified in the context of this invention are number-average).

The polymer which is miscible with the vinyl chloride polymer can be of any nature, with the exception of this polymer itself. It can be a homopolymer or a copolymer. This polymer is said to be miscible with the vinyl chloride polymer when, mixed with the latter, the resulting mixture is single phase, that is to say that it only exhibits a single glass transition temperature, intermediate between the glass transition temperatures of the components of the mixture taken separately.

Mention may be made, in a non-limiting way, among the polymers which are miscible with the vinyl chloride polymer, of certain polyesters, certain polyacrylates or polymethacrylates, certain copolymers of vinyl acetate or of acrylonitrile, and the like. More particularly, aliphatic polyesters and poly(methyl methacrylate) can be used. Very good results have been obtained with poly-ε-caprolactone.

The block of polymer which is miscible with the vinyl chloride polymer can also have any average molecular mass. However, it has been observed that it was preferable to use a block copolymer such that the average molecular mass of the said block is greater than or equal to the average molecular mass of the poly(ethylene oxide) block.

It proved to be particularly advantageous for the average molecular mass of the block of polymer which is miscible with the vinyl chloride polymer to be at least equal to 4000 g/mol.

Although there is generally no upper limit to the average molecular mass of the block of polymer which is miscible with the vinyl chloride polymer, it has been observed that an average molecular mass less than or equal to 30,000 g/mol offered advantageous results. An average molecular mass less than or equal to 20,000 g/mol made possible particularly advantageous results.

It should be noted that the block copolymer can contain, in the same molecule, a number of poly(ethylene oxide) blocks and/or a number of blocks of polymer which is miscible with the vinyl chloride polymer and/or one or more blocks of other natures. Excellent results have been obtained with a two-block copolymer composed of a poly(ethylene oxide) block and of a block of a polymer which is miscible with the vinyl chloride polymer.

The block copolymer can have any average molecular mass. It is advantageously at least 4500 g/mol. Good results have been obtained with an average molecular mass of at least 8500 g/mol. Particularly advantageous results have been obtained with an average molecular mass of at least 10,000 g/mol.

It is quite obvious that, in addition to the vinyl chloride polymer, plasticizer and block copolymer characteristic of the invention, the composition can also comprise other components, polymeric or otherwise. Very good results have been obtained with a composition essentially composed of a vinyl chloride polymer, of a plasticizer and of a block copolymer characteristic of the invention.

In addition, the usual additives, such as stabilizers, lubricants, dyes, pigments, anti-blocking agents, and the like, can be employed.

The block copolymer can be incorporated according to any process known to the person skilled in the art. For example, the block copolymer can be mixed while hot with the vinyl chloride polymer during the final working-up or during an intermediate compounding. Another solution can comprise the introduction of the block copolymer into the mixture for the polymerization of vinyl chloride, during the synthesis of this polymer.

The invention also relates to a block copolymer which can be used in the composition described above and which is characterized in that the block copolymer is a diblock copolymer comprising a poly(ethylene oxide) block with an average molecular mass at least equal to 300 g/mol, preferably at least equal to 500 g/mol, and a poly-ε-caprolactone block with an average molecular mass at least equal to 500 g/mol.

The new diblock copolymer according to the invention corresponds to the general statistical formula

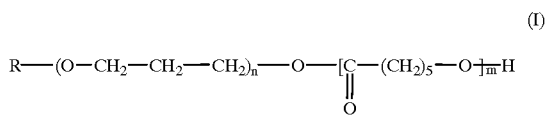

in which R represents a monovalent hydrocarbon radical and n and m represent integers such that the average molecular mass of the poly(ethylene oxide) block is at least equal to 300 g/mol, preferably at least equal to 500 g/mol, and that of the poly-ε-caprolactone block is at least equal to 500 g/mol. The average molecular mass of the poly(ethylene oxide) block is preferably at least equal to 3000 g/mol. That of the poly-ε-caprolactone block is preferably at least equal to 3000 g/mol and more particularly still to 4000 g/mol.

A diblock copolymer of this type which is particularly preferred is that in which the average molecular mass of the poly-ε-caprolactone block is greater than or equal to that of the poly(ethylene oxide) block. The molecular mass of the poly-ε-caprolactone block preferably does not exceed 30,000 g/mol and more particularly 20,000 g/mol. The average molecular mass of the diblock copolymer is advantageously at least 4500 g/mol. It is preferably at least 8500 g/mol and more particularly still at least 10,000 g/mol.

Advantageously, the hydrocarbon radical R which is found in the end position of the poly(ethylene oxide) block is an aliphatic radical (which can be linear, branched or cyclic) or alternatively an aromatic radical. The R— radical preferably represents an aliphatic radical not containing more than 20 carbon atoms. Excellent results have been obtained with a diblock copolymer in which the end radical R of the poly(ethylene oxide) block represents a linear alkyl radical and in particular a methyl radical.

The new diblock copolymer according to the invention can be synthesized by any method known to the person skilled in the art and, in particular, by anionic polymerization of ε-caprolactone in the presence of monohydroxylated poly(ethylene oxide) (R—(O—CH$_2$—CH$_2$)$_n$—OH), with the involvement of organometallic initiators, more particularly organoaluminium or organozinc initiators.

The polymerization initiator is advantageously an organoaluminium or organozinc compound produced in situ by reaction between the monohydroxylated poly(ethylene oxide) and a precursor of the alkylaluminium or alkylzinc type in an at least equimolecular ratio by weight, for example from 1 to 4, in order to produce aluminium or zinc alkoxides. When the monohydroxylated poly(ethylene oxide) is reacted with an equimolar amount of precursor of the alkylaluminium or alkylzinc type, an aluminium or zinc monoalkoxide of general formula:

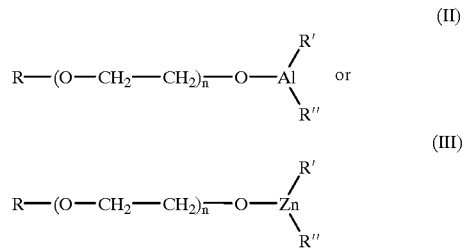

in which R has the meaning provided above and R' and R" represent, independently of one another, a linear or branched alkyl radical, is produced. The hydrocarbon radicals R' and R" advantageously represent, independently of one another, a linear or branched alkyl radical containing from 1 to 16 carbon atoms. Preferably, these radicals are identical and represent a linear or branched alkyl radical containing from 2 to 6 carbon atoms.

One procedure which gives excellent results comprises dissolving monohydroxylated poly(ethylene oxide) (for example poly(ethylene oxide) containing an end methyl radical) with stirring and under nitrogen in the appropriate amount of ε-caprolactone, bringing the solution obtained to a temperature of the order of approximately 80° C. until a homogeneous solution is obtained, cooling the solution to approximately 30–35° C. and then introducing trialkylaluminium (for example triethylaluminium) or dialkylzinc (for example diethylzinc) in an equimolar amount with respect to the monohydroxylated poly(ethylene oxide). Under these conditions, an aluminium monoalkoxide (of general formula II) or a zinc monoalkoxide (of general formula III) is formed in situ and initiates the polymerization of the ε-caprolactone. Degrees of conversion of close to 100% are achieved in a few tens of minutes.

The composition according to the invention in particular has the advantage of substantially preventing the adsorption of organic macromolecules, such as proteins or biological cells, at its surface. An additional advantage is the low desorption of its constituents. Another advantage of the composition according to the invention lies in the improvement in the sliding properties which it provides with respect to usual vinyl chloride polymer flexible compositions. It thus finds its preferred field of application in the production of articles used in the medical profession.

For this reason, another subject of the invention is a use of the composition as described above for the manufacture of an article.

Another subject of the invention is alternatively an article comprising at least one layer composed essentially of a composition as described above. For example, the article can comprise at least one layer of any nature and one layer in contact with the biological medium, the latter being composed essentially of a composition according to the invention.

The article concerned by the present invention can be of any nature. It can be, for example, a hollow body, such as a receptacle or a tubing, or a flat product. In the case of a flat product, films or sheets are preferred.

The article according to the invention can have any field of use; however, it is preferably used in the field of accessories for medical use. Medical use is understood to mean all the applications related to the profession of preserving or of restoring human or animal health. This includes in particular surgery, pharmacology or dentistry. The accessories for medical use can also be of any nature: flat product, receptacle, sheath, tubing or bag, inter alia.

In the case of accessories for medical use, the article is preferably provided in the form of a bag or tubing. The said bag and the said tubing can contain or transport, for example, blood, plasma, various aqueous solutions and any biological fluid in general.

In the case of a tubing, the sliding properties, particularly improved after sterilization with steam or after having been left in a moist atmosphere, are in particular useful for the production of catheters or similar accessories. Likewise, the low adhesion of microbes, in particular of bacteria, is advantageous in the case of catheters, in particular by reducing the risk of inflammation during prolonged use.

EXAMPLES

Example 1, not in accordance with the invention, is given by way of comparison. Examples 2 and 3 illustrate the invention, in a non-limiting way.

Example 1

For Reference 65 g of a Medigranuul® vinyl chloride polymer flexible composition marketed by Draka Polva B.V., of PSV 3250 type, were mixed for 12 minutes in an internal mixer of Brabender® Plastograph® type. The rotational speed of the cams was 50 rev/min and the set temperature for the mixer was 150° C. After mixing, the composition was introduced between the plates of a Schwabenthan® press, which plates had been conditioned for 5 minutes at 170° C. Films with a thickness of 300 μm were obtained by pressing for 5 minutes under a pressure of 200 bars.

Example 2

Example 1 is repeated, with the only difference that 2.6 g of block copolymer are added, in the mixer, to the vinyl chloride polymer flexible composition (i.e. 4 parts of block copolymer per 100 parts of the latter). The block copolymer is composed of a poly(ethylene oxide) block with an average molecular mass equal to 750 g/mol and of a poly-ε-caprolactone block with an average molecular mass equal to 4100 g/mol.

Example 3

Example 2 is repeated, with the only difference that the block copolymer is composed of a poly(ethylene oxide) block with an average molecular mass equal to 5000 g/mol and of a poly-ε-caprolactone block with an average molecular mass equal to 5700 g/mol.

A number of types of tests were carried out in order to evaluate the behaviour of the films arising from the different examples, in particular when they are brought into contact with media commonly used in medical applications.

Exudation of the Block Copolymer

The films were stored at ambient temperature and ambient relative humidity, for 3½ months, between two sheets of white paper. Exudation was evaluated by the possible appearance of translucent or opaque spots or of a translucent or opaque veil on the surface of the films, which are entirely transparent at the start.

Desorption of the Block Copolymer on Contact with Water

A film surface corresponding to 61 cm² was immersed in 25 ml of demineralized water for 24 hours at room temperature and with constant agitation. The amount of block copolymer which has migrated into the water was quantitatively determined by thin layer chromatography, followed by visualization by Dragendorff's reagent (formation of a coloured complex with poly(ethylene oxide)) and measurement of the photodensity at 520 nm. Chromatography took place while using silica of 5729 type from the firm Merck as stationary phase and methylene chloride/acetone (85/15 by volume) and chloroform/methanol (75/25 by volume) mixtures as mobile phases. The results were expressed by weight of block copolymer which has migrated into the aqueous phase.

Adsorption of Proteins

Bovine serum albumin (hereinafter named BSA) solutions labelled with europium were first prepared. Labelling with europium was carried out by mixing a BSA solution (5.5 μg/ml in a 50 mM bicarbonate buffer, of pH=8.53) with a labelling solution (Eu—DTTA—$C_6H_4$—NCS, Delfia® kit of 1244-302 type) and incubation for 24 hours at 4° C. The labelled product was intensively dialysed with distilled water in order to remove any europium not bound to the BSA. The labelled BSA was diluted in a saline phosphate buffer solution.

Discs with a diameter of 12 mm were cut out from the films arising from the different examples. Each of these discs was placed in a cavity in a plate, the surfaces of which were blocked beforehand, with respect to the adsorption of proteins, by contact for 24 hours at 4° C. with a 5% solution of skimmed milk in a saline phosphate buffer. 2 ml of the labelled BSA solution, of given concentration, were added and the whole mixture incubated for 2 hours at 37° C. The discs were then washed at least five times with a 0.02% solution of nonionic Tween® 20 detergent in a phosphate buffer and a further five times with distilled water. After transfer of the discs into the cavities of a clean plate, 1 ml of enhancing solution (supplied with the kit, frees europium) was added to each cavity. The whole array was incubated for 10 minutes at room temperature. 100 µl samples of the enhancing solution were analysed using a Delfia fluorimeter ("time-resolved fluorimetry"). The results were expressed by weight of BSA adsorbed per disc.

Blood Contact 4 ml of human blood and 0.4 ml of aqueous sodium citrate solution (0.129 molar), acting as anticoagulant, were mixed in a closed glass tube. A piece of film (5 cm×0.8 cm), arising from the different examples, was introduced into each tube and, after reclosing, left in contact with the blood for 3 hours at room temperature with slow agitation. The films were then rinsed twice with a 0.09% NaCl solution and the blood platelets bound to the polymer by passing into a 3% glutaraldehyde solution. After drying, the amount of blood platelets adhering to the films was estimated by scanning electron microscopy (magnification 500×).

The results of the different evaluations are combined in Table 1.

TABLE 1

Results of the evaluations

| Evaluation | Example 1 (no block copolymer) | Example 2 | Example 3 |
|---|---|---|---|
| Exudation of the block copolymer | — | very slight | no |
| Desorption of the block copolymer [mg/25 ml] | — | 0.69 | 0.18 |
| Adsorption of proteins [ng of BSA/disc] [BSA]: | | | |
| 100 ng/ml | 0.6 | 0.1 | 0.1 |
| 1000 ng/ml | 3.8 | 1.1 | 0.7 |
| 10,000 ng/ml | 21.3 | 9.7 | 7.5 |
| Blood contact [number of platelets adsorbed] | many | a few aggregates | 0 |

What is claimed is:

1. A flexible composition comprising a vinyl chloride polymer and a block copolymer, said vinyl chloride polymer being a plasticized vinyl chloride polymer comprising at least 20 parts of plasticizer per 100 parts by weight of vinyl chloride polymer, and said plasticizer is different from said block copolymer, and the concentration of the block copolymer is between 0.5 and 10.0 parts per 100 parts by weight of a plasticized vinyl chloride polymer; and the block copolymer is a diblock copolymer comprising a polyethylene oxide block and a block of a poly-ε-caprolactone, and the average molecular mass of the block of poly-ε-caprolactone and the average molecular mass of the polyethylene oxide block each at least equal 3000 g/mol, and the block of poly-ε-caprolactone has an average molecular mass which is greater than or equal to the average molecular mass of the polyethylene oxide block.

2. The composition according to claim 1, wherein the average molecular mass of the block of poly-ε-caprolactone is less than or equal to 30,000 g/mol.

3. In a method of manufacturing an article, the improvement comprising the step of using a composition according to claim 1.

4. An article comprising at least one layer consisting essentially of a composition according to claim 1.

5. The article according to claim 4, in the form of a film or sheet.

6. The article according to claim 4, said article being an accessory for medical use.

7. The article according to claim 6, said article being a bag for medical use.

8. An article for medical use comprising at least one layer made essentially of a flexible composition comprising a vinyl chloride polymer and a block copolymer, said vinyl chloride polymer being a plasticized vinyl chloride polymer comprising at least 20 parts of plasticizer per 100 parts by weight of vinyl chloride polymer, and said plasticizer is different from said block copolymer, and the concentration of the block copolymer is between 0.5 and 10.0 parts per 100 parts by weight of the plasticized vinyl chloride polymer, the block copolymer is selected from copolymers comprising a block of polyethylene oxide and a block of poly-ε-caprolactone, and the average molecular mass of the block of poly-ε-caprolactone and the average molecular mass of the polyethylene oxide block each at least equal 3000 g/mol and the block of poly-ε-caprolactone has an average molecular mass which is greater than or equal to the average molecular mass of the polyethylene oxide block.

* * * * *